US010648361B2

(12) United States Patent
Hagen

(10) Patent No.: US 10,648,361 B2
(45) Date of Patent: May 12, 2020

(54) OIL DEBRIS MONITOR WITH SEQUENTIAL COIL SYSTEM AND ASSOCIATED ALGORITHMS FOR PARTICLE CONFIRMATION

(71) Applicant: UNITED TECHNOLOGIES CORPORATION, Farmington, CT (US)

(72) Inventor: Gregory S. Hagen, Glastonbury, CT (US)

(73) Assignee: UNITED TECHNOLOGIES CORPORATION, Farmington, CT (US)

( * ) Notice: Subject to any disclaimer, the term of this patent is extended or adjusted under 35 U.S.C. 154(b) by 568 days.

(21) Appl. No.: 15/219,335

(22) Filed: Jul. 26, 2016

(65) Prior Publication Data
US 2018/0030850 A1    Feb. 1, 2018

(51) Int. Cl.
*F01D 21/00*  (2006.01)
*G01N 33/28*  (2006.01)
(Continued)

(52) U.S. Cl.
CPC .............. *F01D 21/003* (2013.01); *F02C 3/04* (2013.01); *F02C 7/06* (2013.01); *F16N 29/04* (2013.01);
(Continued)

(58) Field of Classification Search
CPC ........ F01D 21/003; F01D 21/10; F01D 25/18; F02C 3/04; F02C 7/06; F02C 9/28;
(Continued)

(56) References Cited

U.S. PATENT DOCUMENTS 3,382,672 A * 5/1968 French ...................... F02C 9/40
60/243
5,001,424 A * 3/1991 Kellett .................... F16N 29/00
324/204
(Continued)

FOREIGN PATENT DOCUMENTS

DE    102006018964 A1    10/2007
GB         2101330 A      1/1983
(Continued)

OTHER PUBLICATIONS

Electronic Interface for an Inductive Wear Debris Sensor for Detection of Ferrous and Non-Ferrous Particles. A Thesis Presented to the Graduate Faculty of the University of Akron. Joseph P. Davis Dec. 2013.
(Continued)

*Primary Examiner* — Mark A Laurenzi
*Assistant Examiner* — Loren C Edwards
(74) *Attorney, Agent, or Firm* — Carlson, Gaskey & Olds, P.C.

(57) ABSTRACT

A debris monitoring system has a first sensor configured to generate a first signal indicating a presence of a metallic particle in a lubrication system. A second sensor is configured to generate a second signal indicating the presence of a metallic particle in the lubrication system. A signal processor is configured to determine a presence of a metallic particle in a fluid passage based on a comparison of at least the first signal and the second signal; the second signal being used to verify accuracy of the first signal. A gas turbine engine and a method for monitoring a fluid passage for debris are also disclosed.

20 Claims, 8 Drawing Sheets

(51) Int. Cl.
*F16N 29/04* (2006.01)
*F02C 3/04* (2006.01)
*F02C 7/06* (2006.01)
*G01M 15/14* (2006.01)

(52) U.S. Cl.
CPC ........ *G01M 15/14* (2013.01); *G01N 33/2858* (2013.01); *F05D 2220/32* (2013.01); *F05D 2240/35* (2013.01); *F05D 2260/98* (2013.01); *F16N 2250/32* (2013.01)

(58) Field of Classification Search
CPC ...... F16N 29/04; G01M 15/14; F04D 27/001; G01N 33/28; G01N 33/2858; F05D 2220/32; F05D 2240/35; F05D 2260/98; F05D 2250/32
USPC ....................................................... 60/39.08
See application file for complete search history.

(56) References Cited

U.S. PATENT DOCUMENTS

| | | | |
|---|---|---|---|
| 5,811,664 A | 9/1998 | Whittington et al. | |
| 6,752,003 B2 | 6/2004 | Foedisch et al. | |
| 8,235,657 B2 * | 8/2012 | Bulin | F01D 9/065 415/176 |
| 8,816,674 B2 | 8/2014 | Ukai et al. | |
| 9,274,041 B2 | 3/2016 | Henning et al. | |
| 2006/0105467 A1* | 5/2006 | Niksa | G01N 27/126 436/150 |
| 2010/0027006 A1 | 2/2010 | Hertens et al. | |
| 2015/0293009 A1* | 10/2015 | Henning | G01N 15/02 356/72 |

FOREIGN PATENT DOCUMENTS

| | | |
|---|---|---|
| JP | 2016079860 | 5/2016 |
| WO | 2015134602 | 9/2015 |

OTHER PUBLICATIONS

A New Oil Debris Sensor for Online Condition Monitoring of Wind Turbine Gearboxes. Chao Wang, Xiao Liu, Hui Liu and Zhe Chen. Department of Energy Technology, Aalborg University, Aalborg East, 9220, Denmark.
On-line and In-line Wear Debris Detectors: What's Out There? Sabrin Gebarin. A Noria Publication available at: http://www.machinerylubrication.com/Read/521/in-line-wear-debris-detectors.
European Search Report for European Application No. 17182741.3 dated Aug. 22, 2017.

* cited by examiner

OIL DEBRIS MONITOR WITH SEQUENTIAL COIL SYSTEM AND ASSOCIATED ALGORITHMS FOR PARTICLE CONFIRMATION

STATEMENT REGARDING FEDERALLY SPONSORED RESEARCH OR DEVELOPMENT

The subject of this disclosure was made with government support under Contract No.: N00019-02-C-3003 awarded by the United States Navy. The government therefore may have certain rights in the disclosed subject matter.

BACKGROUND

This application relates generally to a debris monitoring system for an oil distribution system.

Gas turbine engines are known and, typically, utilized to drive aircraft. A gas turbine engine typically includes a fan section, a compressor section, a combustor section and a turbine section. Air entering the compressor section is compressed and delivered into the combustion section where it is mixed with fuel and ignited to generate a high-speed exhaust gas flow. The high-speed exhaust gas flow expands through the turbine section to drive the compressor and the fan section. The compressor section typically includes low and high pressure compressors, and the turbine section includes low and high pressure turbines. More recently, gas turbine engines have used gear reductions to allow their fan sections to rotate at different speeds than their turbine sections.

Oil lubrication systems have historically been used to improve the operation of machinery such as gas turbine engines. Metallic debris in an oil lubrication system may indicate impending component failure, so timely discovery of debris in the oil can contribute to the performance and longevity of a machine. Routine manual inspection of oil distribution systems has been employed, but more recently automatic, condition based oil debris monitoring systems have been discovered to be simpler and less time consuming.

One known oil debris monitoring system uses a sensor having a coil on an oil line configured to provide a signal upon detecting a magnetic disruption consistent with metallic debris in the oil line. Such sensors are susceptible to generating false positives because available signal processing technology is sometimes unable to distinguish electromagnetic noise in the environment from debris. Faults in oil debris monitoring system hardware have further contributed to false positive signals.

False positive signals may result in unneeded maintenance downtime.

SUMMARY

In a featured embodiment, a debris monitoring system has a first sensor configured to generate a first signal indicating a presence of a metallic particle in a lubrication system. A second sensor is configured to generate a second signal indicating the presence of a metallic particle in the lubrication system. A signal processor is configured to determine a presence of a metallic particle in a fluid passage based on a comparison of at least the first signal and the second signal; the second signal being used to verify accuracy of the first signal.

In another embodiment according to the previous embodiment, the comparison comprises an assessment of whether a size of a particle indicated by an amplitude of the first signal matches a size of a particle indicated by an amplitude of the second signal.

In another embodiment according to any of the previous embodiments, a third sensor is configured to generate a third signal, and wherein the signal processor is configured to include the third signal in the comparison.

In another embodiment according to any of the previous embodiments, one of the first and second sensors is downstream from the other of the first and second sensors.

In another embodiment according to any of the previous embodiments, the first sensor and second sensor are separated by a known distance and the comparison comprises an assessment of whether the first signal and second signal are separated by an expected delay consistent with a single particle carried by a fluid moving at an expected flow speed.

In another embodiment according to any of the previous embodiments, the signal processor is configured to reject simultaneous indications of the presence of a metallic particle by the first and second signal as erroneous.

In another embodiment according to any of the previous embodiments, the signal processor is configured to calculate an estimated quantity of debris based on the comparison, and to issue a warning if the estimated quantity of debris exceeds a threshold.

In another embodiment according to any of the previous embodiments, the first sensor and second sensor are in a concentric arrangement.

In another featured embodiment, gas turbine engine has a compressor, a combustor, a turbine and a lubrication system. A debris monitoring system has a first sensor configured to generate a first signal indicating a presence of a metallic particle in the lubrication system. A second sensor is configured to generate a second signal indicating the presence of a metallic particle in the lubrication system. A signal processor is configured to determine a presence of a metallic particle in a fluid passage based on a comparison of at least the first signal and the second signal; the second signal being used to verify accuracy of the first signal.

In another embodiment according to the previous embodiment, one of the first and second sensor is downstream from the other of the first and second sensor.

In another embodiment according to any of the previous embodiments, the first sensor and second sensor are separated by a known distance and the comparison comprises an assessment of whether the first signal and second signal are separated by an expected delay consistent with a single particle carried by a fluid moving at an expected flow speed.

In another embodiment according to any of the previous embodiments, the comparison comprises an assessment of whether a size of a particle indicated by an amplitude of the first signal matches a size of a particle indicated by an amplitude of a the second signal.

In another embodiment according to any of the previous embodiments, the signal processor is configured to reject simultaneous indications of the presence of a metallic particle by the first signal and second signal as erroneous.

In another featured embodiment, a method for monitoring a fluid passage for debris including receiving a first signal from a first sensor indicating a presence of a metallic particle, checking for a second signal from a second sensor indicating the presence of the metallic particle, and if a second signal exists, using the second signal to verify an accuracy of the first signal.

In another embodiment according to the previous embodiment, a quantity of debris in the fluid passage is estimated.

In another embodiment according to any of the previous embodiments, a warning is issued if the estimated quantity of debris in the fluid passage exceeds a threshold.

In another embodiment according to any of the previous embodiments, a third signal is used to verify accuracy of at least one of the first signal and second signal.

In another embodiment according to any of the previous embodiments, the first sensor and second sensor are separated by a known distance and the verifying comprises assessing whether the first signal and second signal are separated by an expected delay consistent with a single particle carried by a fluid moving at an expected flow speed.

In another embodiment according to any of the previous embodiments, the verifying includes assessing whether a size of a particle indicated by an amplitude of the first signal matches a size of a particle indicated by an amplitude of the second signal.

In another embodiment according to any of the previous embodiments, the verifying comprises rejecting simultaneous indications of the presence of a metallic particle by the first signal and second signal as erroneous.

Although the different examples have the specific components shown in the illustrations, embodiments of this disclosure are not limited to those particular combinations. It is possible to use some of the components or features from one of the examples in combination with features or components from another one of the examples.

These and other features disclosed herein can best be understood from the following specification and drawings, the following of which is a brief description.

DETAILED DESCRIPTION

Figure 1A:
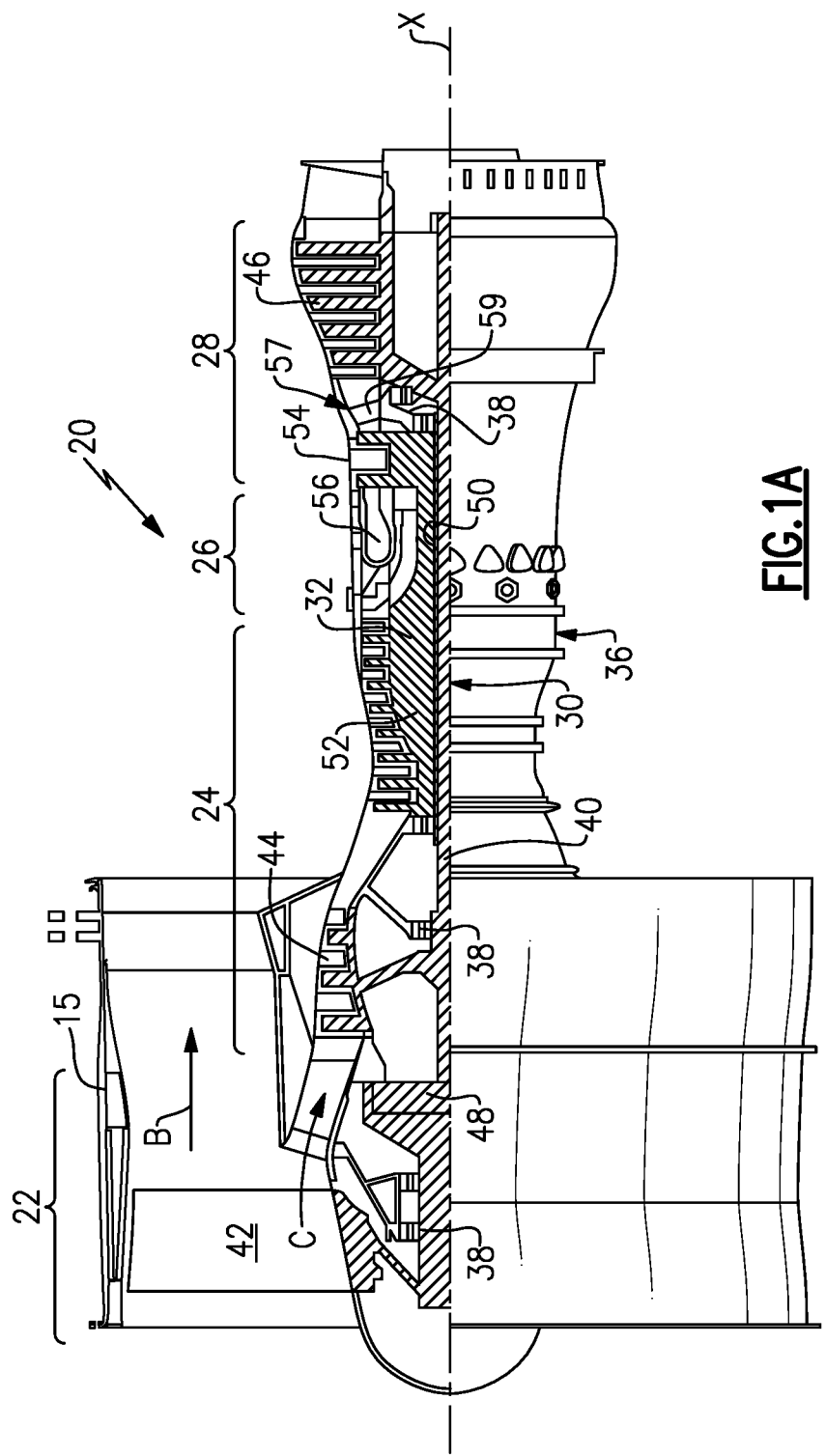
FIG. 1A schematically shows an embodiment of a commercial gas turbine engine.

FIG. 1A schematically illustrates a gas turbine engine 20 as typically used in a commercial aircraft. The gas turbine engine 20 is disclosed herein as a two-spool turbofan that generally incorporates a fan section 22, a compressor section 24, a combustor section 26 and a turbine section 28. Alternative engines might include an augmenter section (not shown) among other systems or features. The fan section 22 drives air along a bypass flow path B in a bypass duct defined within a nacelle 15, while the compressor section 24 drives air along a core flow path C for compression and communication into the combustor section 26 then expansion through the turbine section 28. Although depicted as a two-spool turbofan gas turbine engine in the disclosed non-limiting embodiment, it should be understood that the concepts described herein are not limited to use with two-spool turbofans as the teachings may be applied to other types of turbine engines including three-spool architectures.

The exemplary engine 20 generally includes a low speed spool 30 and a high speed spool 32 mounted for rotation about an engine central longitudinal axis X relative to an engine static structure 36 via several bearing systems 38. It should be understood that various bearing systems 38 at various locations may alternatively or additionally be provided, and the location of bearing systems 38 may be varied as appropriate to the application.

The low speed spool 30 generally includes an inner shaft 40 that interconnects a fan 42, a first (or low) pressure compressor 44 and a first (or low) pressure turbine 46. The inner shaft 40 is connected to the fan 42 through a speed change mechanism, which in exemplary gas turbine engine 20 is illustrated as a geared architecture 48 to drive the fan 42 at a lower speed than the low speed spool 30. The high speed spool 32 includes an outer shaft 50 that interconnects a second (or high) pressure compressor 52 and a second (or high) pressure turbine 54. A combustor 56 is arranged in exemplary gas turbine 20 between the high pressure compressor 52 and the high pressure turbine 54. A mid-turbine frame 57 of the engine static structure 36 is arranged generally between the high pressure turbine 54 and the low pressure turbine 46. The mid-turbine frame 57 further supports bearing systems 38 in the turbine section 28. The inner shaft 40 and the outer shaft 50 are concentric and rotate via bearing systems 38 about the engine central longitudinal axis X which is collinear with their longitudinal axes.

The core airflow is compressed by the low pressure compressor 44 then the high pressure compressor 52, mixed and burned with fuel in the combustor 56, then expanded over the high pressure turbine 54 and low pressure turbine 46. The mid-turbine frame 57 includes airfoils 59 which are in the core airflow path C. The turbines 46, 54 rotationally drive the respective low speed spool 30 and high speed spool 32 in response to the expansion. It will be appreciated that each of the positions of the fan section 22, compressor section 24, combustor section 26, turbine section 28, and fan drive gear system 48 may be varied. For example, gear system 48 may be located aft of combustor section 26 or even aft of turbine section 28, and fan section 22 may be positioned forward or aft of the location of gear system 48.

The engine 20 in one example is a high-bypass geared aircraft engine. In a further example, the engine 20 bypass ratio is greater than about six (6), with an example embodiment being greater than about ten (10), the geared architecture 48 is an epicyclic gear train, such as a planetary gear system or other gear system, with a gear reduction ratio of greater than about 2.3 and the low pressure turbine 46 has a pressure ratio that is greater than about five. In one disclosed embodiment, the engine 20 bypass ratio is greater than about ten (10:1), the fan diameter is significantly larger than that of the low pressure compressor 44, and the low pressure turbine 46 has a pressure ratio that is greater than about five 5:1. Low pressure turbine 46 pressure ratio is pressure measured prior to inlet of low pressure turbine 46 as related to the pressure at the outlet of the low pressure turbine 46 prior to an exhaust nozzle. The geared architecture 48 may be an epicycle gear train, such as a planetary gear system or other gear system, with a gear reduction ratio of greater than about 2.3:1. It should be understood, however, that the above parameters are only exemplary of one embodiment of a geared architecture engine and that the present invention is applicable to other gas turbine engines including direct drive turbofans.

A significant amount of thrust is provided by the bypass flow B due to the high bypass ratio. The fan section 22 of the engine 20 is designed for a particular flight condition—typically cruise at about 0.8 Mach and about 35,000 feet (10,668 meters). The flight condition of 0.8 Mach and 35,000 ft (10,668 meters), with the engine at its best fuel consumption—also known as "bucket cruise Thrust Specific Fuel Consumption ('TSFC')"—is the industry standard parameter of lbm of fuel being burned divided by lbf of thrust the engine produces at that minimum point. "Low fan pressure ratio" is the pressure ratio across the fan blade alone, without a Fan Exit Guide Vane ("FEGV") system. The low fan pressure ratio as disclosed herein according to one non-limiting embodiment is less than about 1.45. "Low corrected fan tip speed" is the actual fan tip speed in ft/sec divided by an industry standard temperature correction of [(Tram ° R)/(518.7° R)]$^{0.5}$. The "Low corrected fan tip speed" as disclosed herein according to one non-limiting embodiment is less than about 1150 ft/second (350.5 meters/second).

Figure 1B:
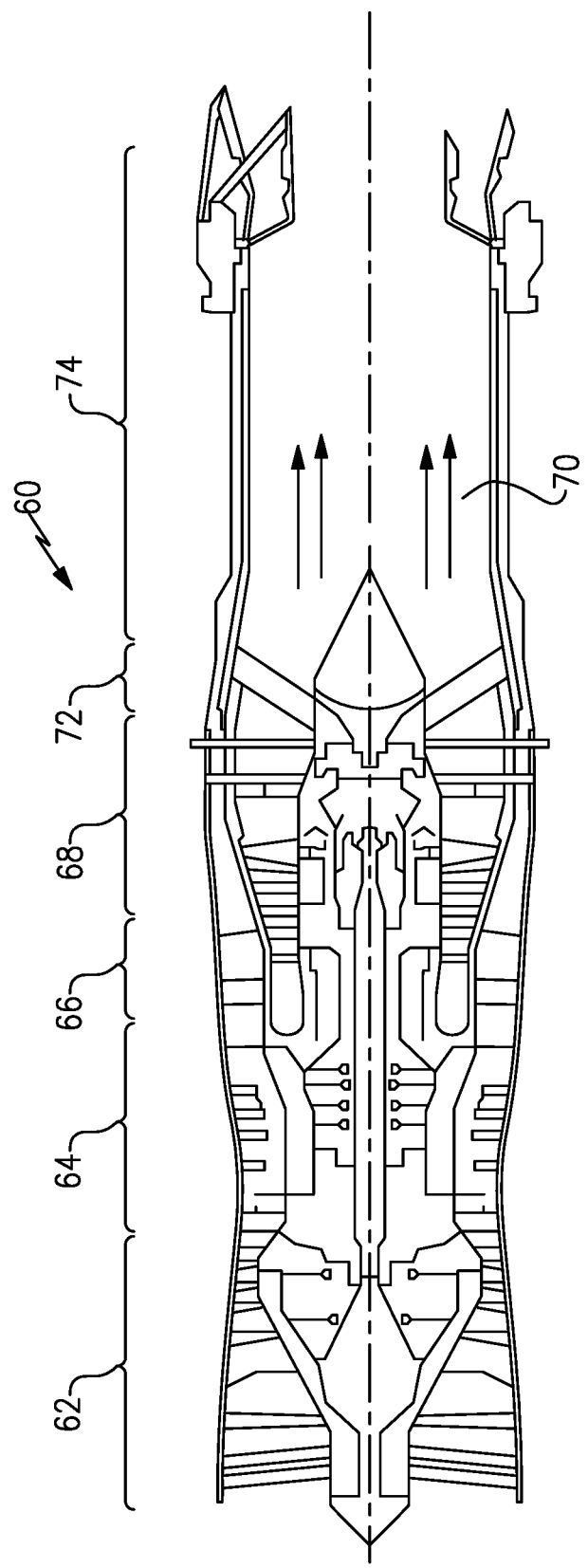
FIG. 1B schematically shows an embodiment of a military gas turbine engine.

Referring to FIG. 1B, a gas turbine engine 60 as may be used in a military application includes a fan section 62, a compressor section 64, a combustor section 66, and a turbine section 68. Air entering into the fan section 62 is initially compressed and fed to the compressor section 64. In the compressor section 64, the incoming air from the fan section 62 is further compressed and communicated to the combustor section 66. In the combustor section 66, the compressed air is mixed with gas and ignited to generate a hot exhaust stream 70. The hot exhaust stream 70 is expanded through the turbine section 68 to drive the fan section 62 and the compressor section 64. In this example, the gas turbine engine 60 includes an augmenter section 72 where additional fuel can be mixed with the exhaust gasses 70 and ignited to generate additional thrust. The exhaust gasses 70 flow from the turbine section 68 and the augmenter section 72 through an exhaust liner assembly 74.

Figure 2:
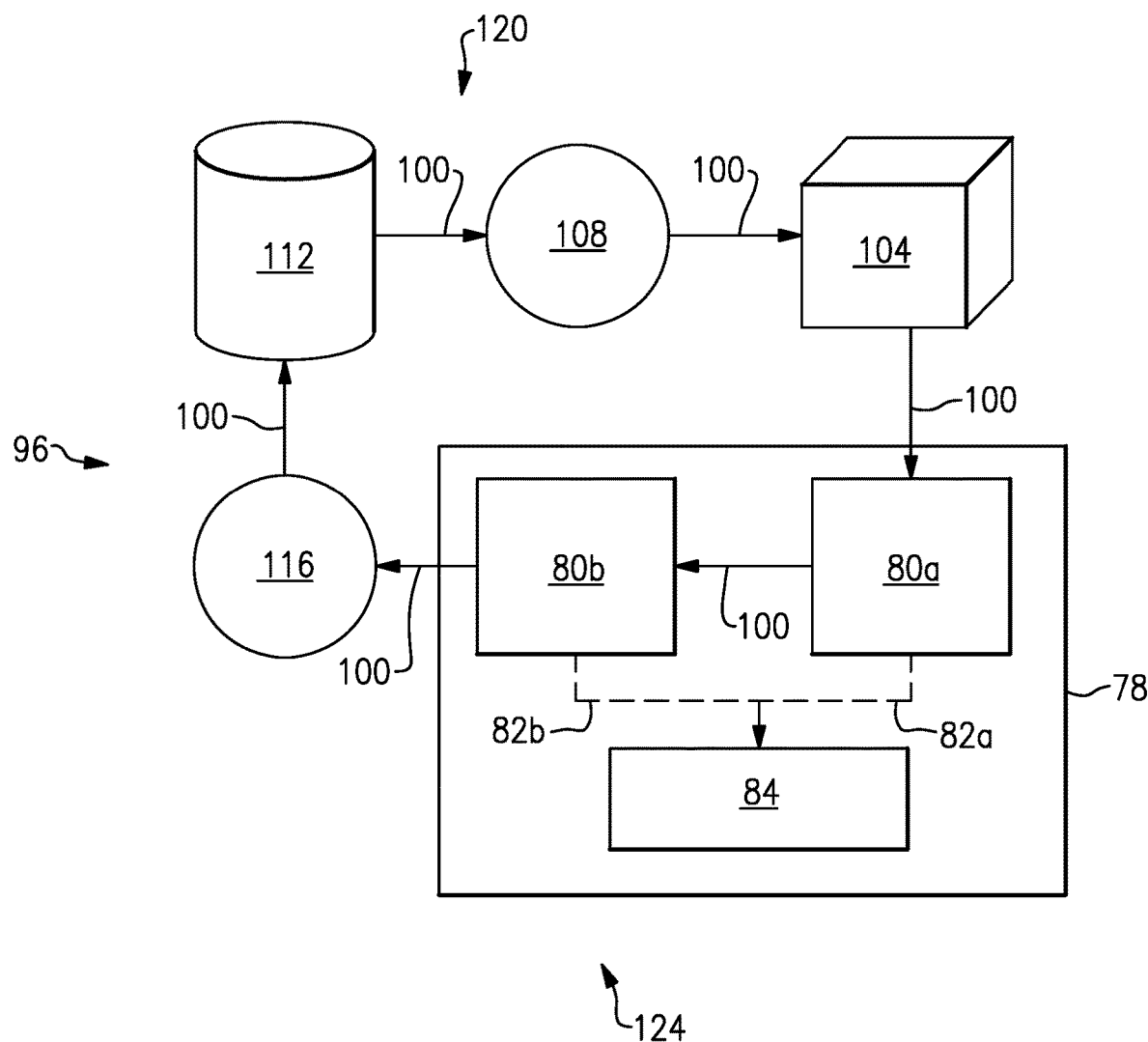
FIG. 2 is a schematic representation of a fluid distribution system.

According to an embodiment of the disclosed invention, a gas turbine engine 20 or 60 has a lubrication system such as a fluid distribution system 96 with a series of fluid passages 100, shown in FIG. 2. In one embodiment, the fluid distribution system 96 distributes oil. Fluid is supplied to machinery 104 through fluid passages 100 by a supply pump 108 from a reservoir 112. The fluid is then extracted from the machinery 104 by a scavenge pump 116 and returned to the reservoir 112. From the schematic representation of FIG. 2 it can be appreciated that the fluid distribution system 96 can be considered to have a supply side 120, where fluid flows from the reservoir 112 to the machinery 104, and a scavenge side 124, where the fluid flows from the machinery 104 to the reservoir 112. The fluid distribution system 96 has a debris monitoring system 78 with sequential sensors 80a and 80b operating in tandem. The first sensor 80a and second sensor 80b send a first signal 82a and a second signal 82b respectively to a signal processor 84, which uses particle detection algorithms to process the signals 82a and 82b for the purpose of determining the presence of debris in the system. The first sensor 80a and the second sensor 80b are connected by the fluid passage. FIG. 2 shows the debris monitoring system 78 on the scavenge side 124 of the fluid distribution system 96, but the debris monitoring system 78 could be located on the supply side 120 or anywhere else as long as they are connected in serial flow such that the second sensor 80b may be used to verify signals from the first sensor 80a.

This fluid distribution system 96 provides lubrication to machinery 104 with moving parts. In one example, the machinery 104 may be a gear reduction, such as gear system 48 of FIG. 1A or other gearbox or bearing system. In an alternate embodiment, the machinery may include other gears or bearings such as gear boxes and bearings in the military engine 60 of FIG. 1B. These may also be within the definition of machinery 104. In another example, the machinery 104 may include a bearing chamber. In yet another example, the machinery 104 includes a pump. A worker of ordinary skill in this art would recognize that the machinery 104 could include any apparatus that would benefit from a supply of fluid lubricant.

Figure 3A:
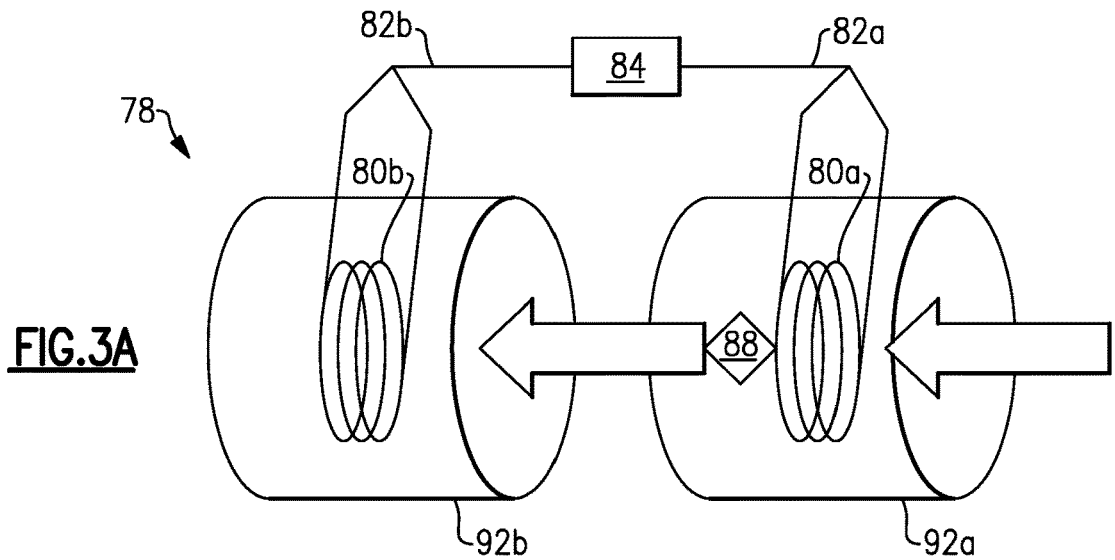
FIG. 3A schematically shows a debris monitoring system according to one embodiment.
Figure 3B:
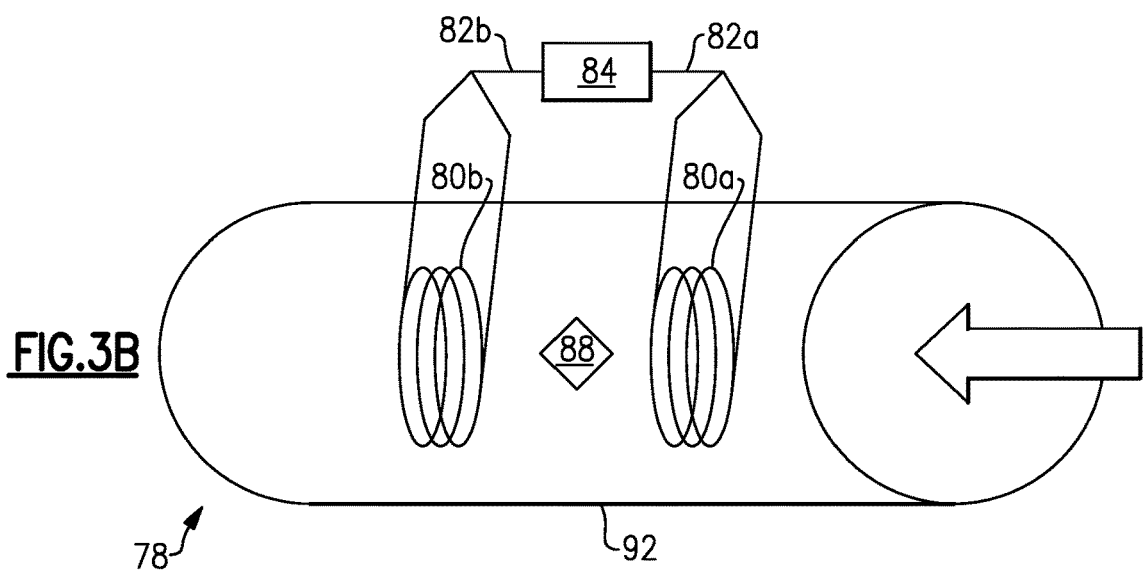
FIG. 3B schematically shows a debris monitoring system according to another embodiment.

As shown in FIG. 3A, sensors 80a and 80b are connected in serial flow. The second sensor 80b is downstream from the first sensor 80a such that when debris or a metallic particle 88 passes by the first sensor 80a it will subsequently pass by the second sensor 80b. Both sensors 80a, 80b, may be known sensors able to detect a metallic particle 88 passing nearby. In an embodiment, at least one of the sensors 80a, 80b has a field generating coil and a particle sensing coil. According to one embodiment, both sensors 80a and 80b are the same type of sensor, but according to a different embodiment they are different types of sensors. The sensors 80a, 80b each measure a condition at their respective location. When a metallic particle 88 passes one of the sensors 80a, 80b, the particle 88 will cause a transient change or disturbance in the condition measured by the sensors 80a, 80b.

In one embodiment, the sensors 80a and 80b are independent sensors in tandem and in separate housings 92a and 92b as shown in FIG. 2A. In another embodiment, the sensors 80a, 80b are two embedded sensing coils in tandem and are enclosed in a common housing 92 as shown in FIG. 2B. In an embodiment, the sensors 80a and 80b are separated by a known distance.

Figure 4:
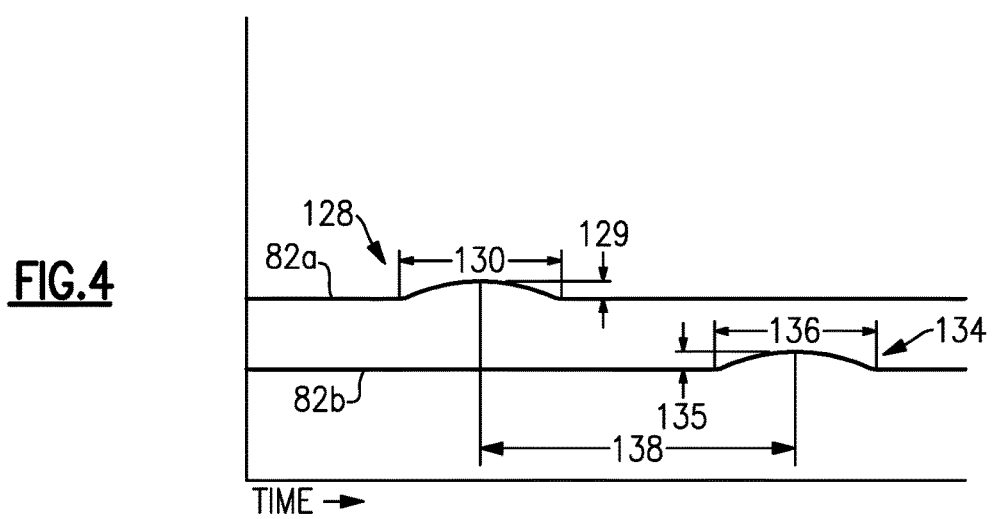
FIG. 4 is a plot showing signals from sensors.

FIG. 4 is a plot of a first measurement 86a and second measurement 86b measured by the first sensor 80a and second sensor 80b, respectively. The first signal 82a and second signal 82b describe at least a portion of the first measurement 86a and the second measurement 86b respectively to the signal processor 84. In an embodiment, the portion includes the time and waveform of a disturbance 128, 134. When debris such as a particle 88 passes sensors 80a, 80b, disturbances 128, 134 in measurements 86a, 86b are detected. The plot shows a first disturbance 128 in the first measurement 86a. As can be appreciated, the first disturbance 128 has a waveform with a shape, an amplitude 129, and a length 130. Likewise, a second disturbance 134 in the second measurement 86b also has a waveform with a shape, an amplitude 135, and a length 136.

In an embodiment, the sensors 80a, 80b each have a discrete local processor that monitors their respective measurements 86a, 86b for disturbances 128, 134 indicative of a metallic particle 88 in the fluid passage 100. Upon finding such a disturbance 128, 134, the sensor 80a, 80b will send a signal 82a, 82b to the signal processor 84. In this embodiment, if the signal processor 84 receives a first signal 82a but never receives a second signal 82b, the signal processor 84 can determine that the first signal 82a was erroneous. In this embodiment, the signals 82a, 82b carry details about their respective disturbances 128, 134. This allows the signal processor 84 to make a comparison of the first signal 82a and the second signal 82b if the signal processor 84 receives both. From the comparison, the signal processor 84 can make a determination about the presence of debris in the fluid passage 100 likely to be more accurate than a determination based on only one signal 82 from only one sensor 80.

In another embodiment, the signal processor 84 receives the signals 82a, 82b continuously. In this embodiment, the signal processor 84 monitors the measurements 86a, 86b through the signals 82a, 82b and the signal processor 84 identifies the disturbances 128, 134.

Using an algorithm, the signal processor 84 can verify accuracy of the first signal 82a in light of the presence or absence of a second signal 82b, the information contained within a second signal 82b, or the timing of a second signal 82b.

Figure 5A:
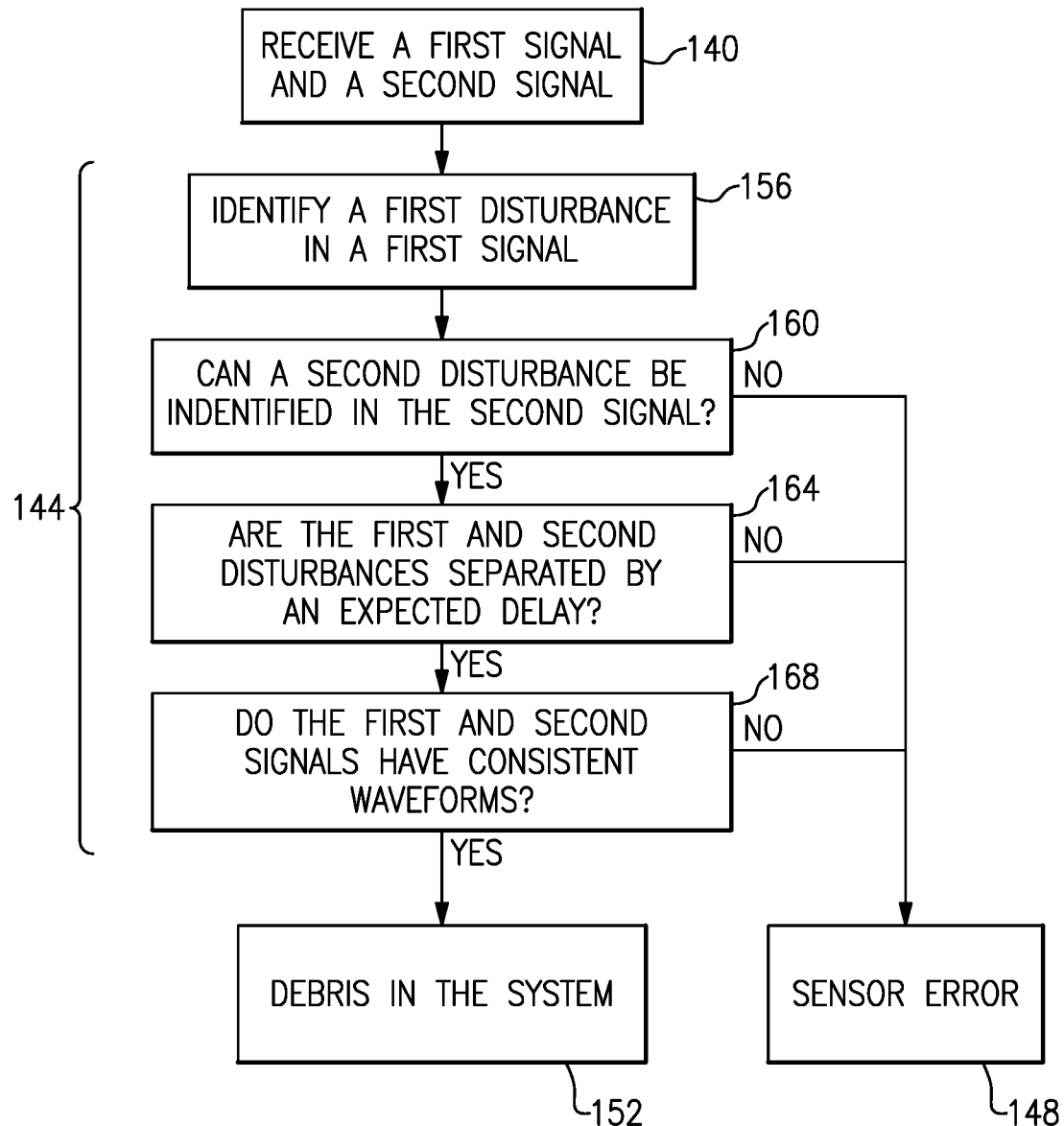
FIG. 5A shows a flowchart of a comparison of signals.

FIG. 5A shows an example process or algorithm for comparing the first signal 82a and second signal 82b. The example process involves the step 140 of receiving at least a first signal 82a and possibly a second signal 82b followed by the step 144 of verifying the first signal 82a. The step 144 of verifying involves seeking confirmation of the first signal 82a from the second signal 82b. The process concludes by reaching either a determination 148 of sensor error or a determination 152 of debris in the system. The step 144 of verification may include several other steps, such as a step 156 of identifying a first disturbance 128. In embodiments where a discrete local processor in the first sensor 80a identifies the first disturbance 128, the step 156 of identifying a first disturbance will occur before the step 140 of receiving signals and outside the step 144 of verifying the first signal 82a.

In an example, the step 144 of verifying includes a step 160 of inquiring as to the presence of a second disturbance 134. If the signal processor 84 does not receive a second signal 82b indicative of a disturbance 134, a determination 148 of sensor error can be reached.

In some embodiments the signal processor 84 may use a flow rate of the fluid to further refine its comparison. In some embodiments, the flow rate of the fluid is detected by a flow rate sensing system. In other embodiments, the flow rate of the fluid is approximated in view of the functional limits of the fluid distribution system 96. The signal processor 84 could estimate an expected delay 138 between when a particle 88 carried by fluid moving at the flow rate would pass a first sensor 80a and second sensor 80b. The step 144 of verifying may include a step 164 of assessing whether the first disturbance 128 and the second disturbance 134 are separated by the expected delay 138. If the second disturbance 134 occurs too soon or too late after the first disturbance 128, a determination 148 of sensor error can be reached. For example, if the first disturbance 128 and second disturbance 134 occur simultaneously, the signal processor 84 can conclude that at least one of the sensors 80a or 80b delivered a false positive.

In some embodiments, the signal processor 84 can examine the waveforms of the first disturbance 128 and second disturbance 134 to draw conclusions about characteristics of a particle 88 that could have cause the disturbances 128, 134. In an example, the shapes, amplitudes 129, 135, or lengths 130, 136 of the disturbances 128, 134 are compared. If a step 168 of comparing the waveforms finds that the first disturbance 128 and second disturbance 134 are consistent such that they seem to have been caused by a particle 88 having the same characteristics, a determination 152 of debris in the system could be reached. In the alternative, if the first disturbance 128 and second disturbance 134 seem to be results of dissimilar particles 88, a determination 148 of sensor error could be reached. The signal processor 84 could interpret a determination 148 of sensor error here to mean that no particle 88 exists, or that a particle 88 does exist but has characteristics between what the first disturbance 128 or second disturbance 134 alone would indicate.

It should be understood that the steps 156, 160, 164, 168 within the step 144 of verification could be conducted in a different order than described above, or a step 144 of verification could involve fewer than all of the steps 156, 160, 164, 168 described above without departing from the scope of the disclosure. In an example, the step 168 of comparing waveforms is conducted before or at the same time as the step 164 of assessing whether the first disturbance 128 and second disturbance 134 are separated by an expected delay 138. In another example, the step 168 of comparing the waveforms is not conducted at all. Further, different steps 156, 160, 164, 168 within the step 144 of verification may be performed by different processors. For example, in an embodiment, the first sensor 80a has a discrete local processor that performs the step 156 of identifying the first disturbance 128 and the second sensor 80b has a discrete local processor that identifies the second disturbance. In this embodiment, the step 156 of identifying a first disturbance 128 in the first signal 82a will occur before the step 140 of receiving signals and outside the step 144 of verifying the first signal 82a.

Figure 5B:
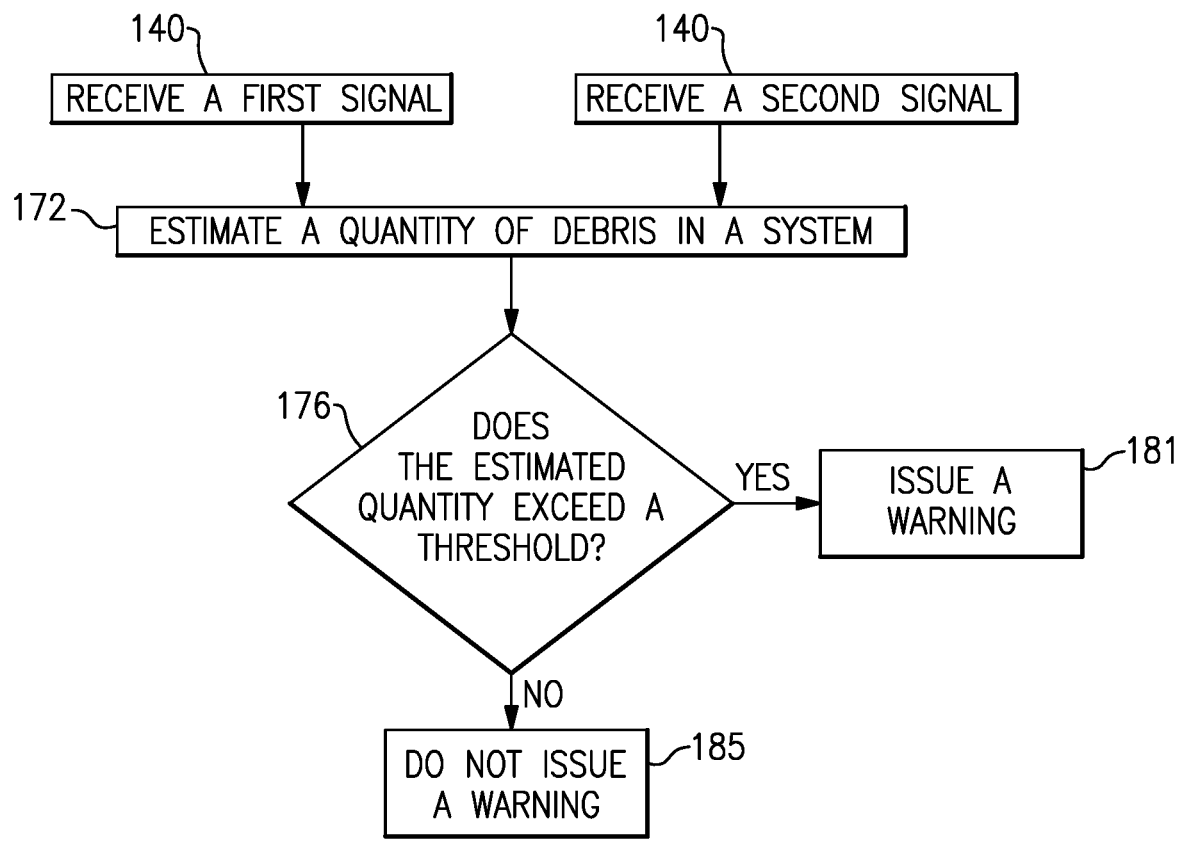
FIG. 5B shows a flowchart of a determination of whether to issue a warning.

In an embodiment, the signal processor 84 can issue a warning according to a process shown in FIG. 5B. The signal processor 84 uses the comparison of the signals 82a and 82b to track individual particles 88 for a step 172 of estimating a total quantity of debris or debris content. The signal processor then conducts the step 176 of comparing the estimated quantity of debris to a threshold. The signal processor 84 issues 181 a warning if the total debris content exceeds the threshold and does not issue 185 a warning if the debris content does not exceed the threshold. In an embodiment, the warning is an indication that maintenance is suggested. For example, the warning could indicate that part of the machinery 104 lubricated by the fluid distribution system 96 is failing.

Figure 6:
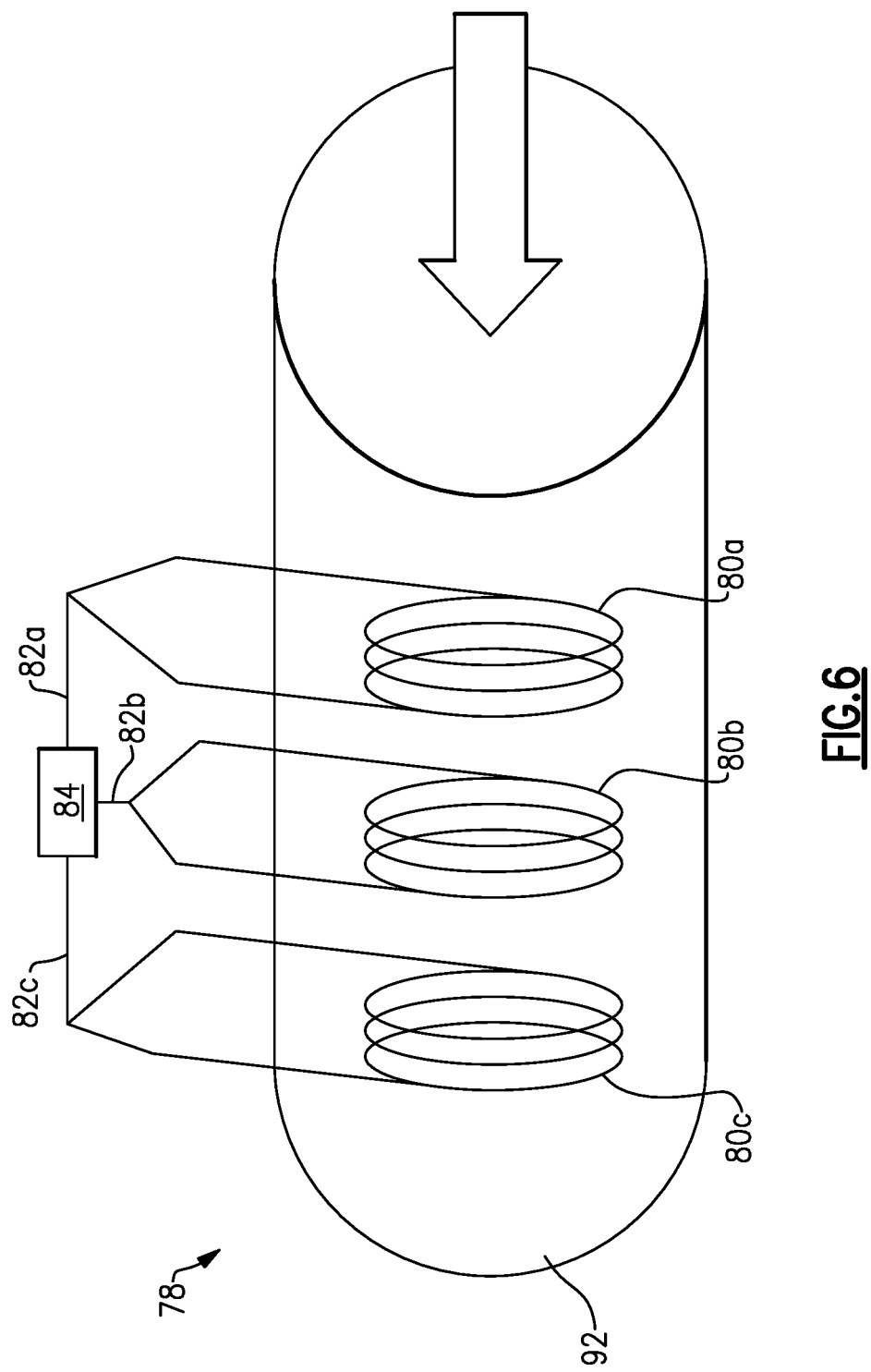
FIG. 6 schematically shows a debris monitoring system according to a third embodiment.

An additional embodiment shown in FIG. 6 has a third sensor 80c. The third sensor 80c sends a third signal 82c that the signal processor 84 can use to further refine its results. A debris monitoring system 78 could have even more sensors without departing from the scope of the disclosure.

Figure 7A:
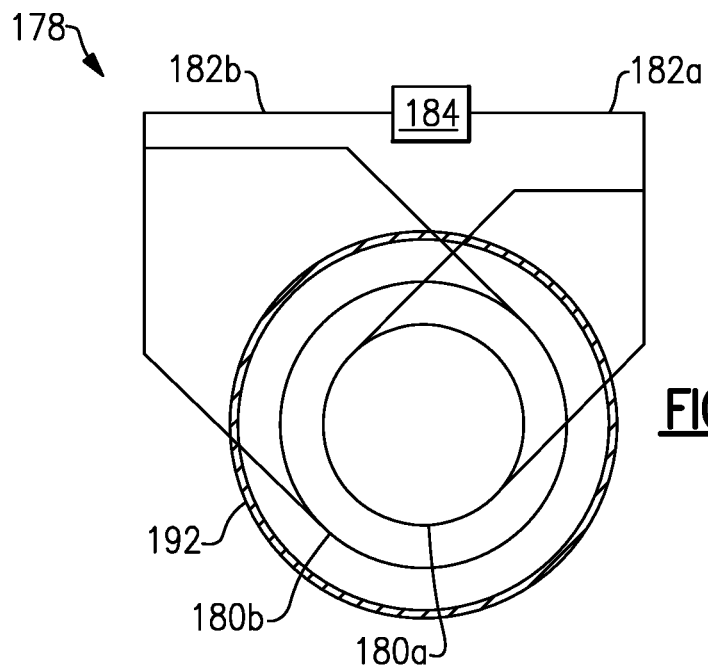
FIG. 7A schematically shows a debris monitoring system according to a fourth embodiment.
Figure 7B:
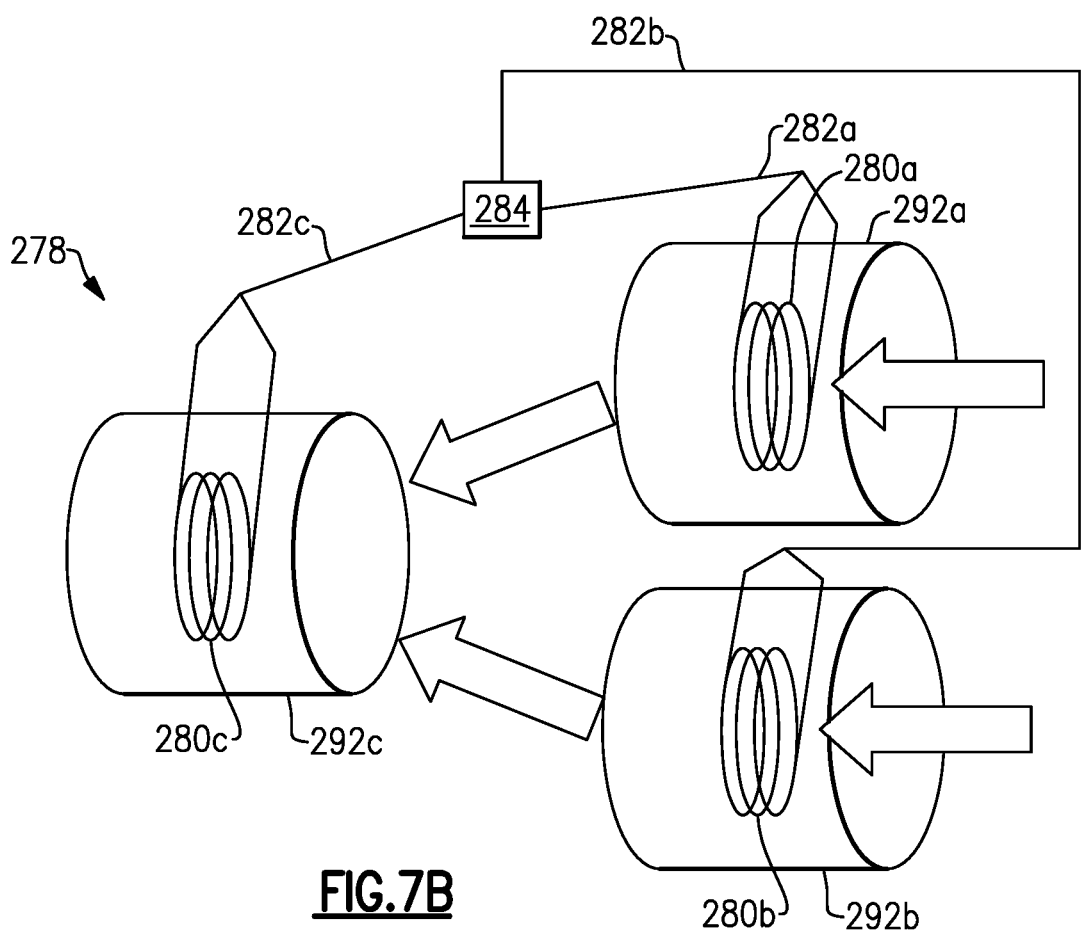
FIG. 7B schematically shows a debris monitoring system according to a fifth embodiment.

While the downstream sensor 80b is disclosed as used to verify the upstream sensor's 80a signal 82a, the upstream sensor 80a could alternatively be used to verify the downstream sensor's 80b signal 80b. Further, though the sensors 80a, 80b are depicted as serially connected in relatively upstream and downstream locations, the sensors 80a, 80b could be at the same location without departing from the scope of the disclosure. In an example embodiment of a debris monitoring system 178 depicted in FIG. 7A, a first sensor 180a and second sensor 180b are arranged concentrically at the same location in a housing 192. The first sensor 180a and second sensor 180b communicate a first signal 182a and second signal 182b, respectively, to a signal processor 184. In another example debris monitoring system 278 depicted in FIG. 7B, a first sensor 280a and second sensor 280b are arranged in parallel and followed by a third sensor 280c. The first sensor 280a, second sensor 280b, and third sensor 280c are respectively embedded in a first housing portion 292a, a second housing portion 292b, and third housing portion 292c. Fluid passing the first sensor 280a or second sensor 280b is communicated to the third sensor 280c enabling a signal processor 284 to use a third signal 282c to verify accuracy of a first signal 282a and second signal 282b.

The signal 82a, 82b could be a discrete signal and only generated when a particle 88 passes. Alternatively, the signal 82a, 82b could be generated continuously, and a disturbance 128, 134 could be generated by a particle 88.

While the embodiments shown above are in a gas turbine engine, the system disclosed herein may have applications in other lubrication applications.

Although an example embodiment has been disclosed, a worker of ordinary skill in this art would recognize that certain modifications would come within the scope of this disclosure. For that reason, the following claims should be studied to determine the scope and content of this disclosure.

The invention claimed is:

1. A debris monitoring system comprising:
a first sensor configured to generate a first signal indicating a presence of a metallic particle in an oil fluid passage of a lubrication system on a gas turbine engine as the metallic particle passes the first sensor;
a second sensor configured to generate a second signal indicating the presence of the metallic particle in the oil fluid passage as the metallic particle passes the second sensor, the first and second sensors are arranged in the oil fluid passage; and
a signal processor configured to determine whether the metallic particle is present in the oil fluid passage based on a comparison of at least the first signal and the second signal; the second signal being used to verify accuracy of the first signal.

2. The debris monitoring system of claim 1, wherein the comparison comprises an assessment of whether a size of a particle indicated by an amplitude of said first signal matches a size of a particle indicated by an amplitude of said second signal.

3. The debris monitoring system of claim 1, further comprising a third sensor configured to generate a third signal, and wherein the signal processor is configured to include the third signal in the comparison.

4. The debris monitoring system of claim 1, wherein one of said first and second sensors is downstream from the other of said first and second sensors.

5. The debris monitoring system of claim 4, wherein the first sensor and second sensor are separated by a known distance and the comparison comprises an assessment of whether the first signal and second signal are separated by an expected delay consistent with a single particle carried by a fluid moving at an expected flow speed.

6. The debris monitoring system of claim 1, wherein the signal processor is configured to reject simultaneous indications of the presence of the metallic particle by the first and second signal as erroneous.

7. The debris monitoring system of claim 1, wherein the signal processor is configured to calculate an estimated quantity of debris based on the comparison, and to issue a warning if the estimated quantity of debris exceeds a threshold.

8. The debris monitoring system of claim 1, wherein the first sensor and second sensor are in a concentric arrangement at a same position along the fluid passage.

9. A gas turbine engine comprising:
a compressor;
a combustor;
a turbine;
a lubrication system having an oil fluid passage; and
a debris monitoring system comprising:
a first sensor configured to generate a first signal indicating a presence of a metallic particle in the oil fluid passage as the metallic particle passes the first sensor;
a second sensor configured to generate a second signal indicating the presence of the metallic particle in the oil fluid passage as the metallic particle passes the second sensor, the first and second sensors are arranged in the oil fluid passage; and
a signal processor configured to determine whether the metallic particle is present in the oil fluid passage based on a comparison of at least the first signal and the second signal; the second signal being used to verify accuracy of the first signal.

10. The gas turbine engine of claim 9, wherein one of said first and second sensor is downstream from the other of said first and second sensor.

11. The gas turbine engine of claim 9, wherein the first sensor and second sensor are separated by a known distance and the comparison comprises an assessment of whether the first signal and second signal are separated by an expected delay consistent with a single particle carried by a fluid moving at an expected flow speed.

12. The gas turbine engine of claim 9, wherein the comparison comprises an assessment of whether a size of a particle indicated by an amplitude of said first signal matches a size of a particle indicated by an amplitude of said second signal.

13. The gas turbine engine of claim 9, wherein the signal processor is configured to reject simultaneous indications of the presence of the metallic particle by the first signal and second signal as erroneous.

14. A method for monitoring an oil fluid passage for debris, comprising:
receiving a first signal from a first sensor arranged in the oil fluid passage indicating a presence of a metallic particle in the oil fluid passage of a lubrication system on a gas turbine engine as the metallic particle passes the first sensor;
checking for a second signal from a second sensor arranged within the oil fluid passage indicating the presence of the metallic particle, the second sensor configured to generate the second signal indicating the presence of the metallic particle in the oil fluid passage as the metallic particle passes the second sensor; and
if the second signal exists, using the second signal to verify an accuracy of the first signal.

15. The method for monitoring an oil fluid passage for debris as recited in claim 14, further comprising estimating a quantity of debris in the fluid passage.

16. The method for monitoring an oil fluid passage for debris of claim 15, further comprising issuing a warning if the estimated quantity of debris in the fluid passage exceeds a threshold.

17. The method for monitoring an oil fluid passage for debris of claim 14, further comprising using a third signal to verify accuracy of at least one of the first signal and second signal.

18. The method for monitoring an oil fluid passage for debris of claim 14, wherein the first sensor and second sensor are separated by a known distance and the verifying comprises assessing whether the first signal and second signal are separated by an expected delay consistent with a single particle carried by a fluid moving at an expected flow speed.

19. The method for monitoring an oil fluid passage for debris of claim 14, wherein the verifying includes assessing whether a size of a particle indicated by an amplitude of the first signal matches a size of a particle indicated by an amplitude of the second signal.

20. The method for monitoring an oil fluid passage for debris of claim 14, wherein the verifying comprises rejecting simultaneous indications of the presence of the metallic particle by the first signal and second signal as erroneous.

* * * * *